United States Patent [19]

Joshi

[11] Patent Number: 5,997,821

[45] Date of Patent: Dec. 7, 1999

[54] GAS AMPLIFIER

[75] Inventor: Ashok V. Joshi, Salt Lake City, Utah

[73] Assignee: Ceramatec Corporation, Salt Lake, Utah

[21] Appl. No.: 08/908,451

[22] Filed: Aug. 7, 1997

Related U.S. Application Data

[63] Continuation of application No. 08/483,384, Jun. 7, 1995, abandoned.

[51] Int. Cl.$^6$ .......................................................... B01J 4/02
[52] U.S. Cl. ............................................................ 422/129
[58] Field of Search ............................................. 422/129

[56] References Cited

U.S. PATENT DOCUMENTS

| | | | |
|---|---|---|---|
| 3,894,538 | 7/1975 | Richter .................................. | 128/260 |
| 4,900,683 | 2/1990 | Metzger et al. ........................ | 436/179 |
| 4,902,278 | 2/1990 | Maget et al. ............................ | 604/132 |

*Primary Examiner*—Timothy McMahon
*Attorney, Agent, or Firm*—Factor and Shaftal

[57] ABSTRACT

A fluid delivery device (10) operated by a first gas delivery device (12) (e.g. electrochemical pump) that takes advantage of sequential gas production methods. The fluid delivery device includes a container (14) with an interior surface. An first gas delivery device for producing or delivering a first gas is placed in one end of the container. A moveable member (e.g. piston, bladder (18) or membrane) is positioned within the container, which moveable member, together with the container's interior surface and the electrochemical cell, structurally define a fluid-tight chamber. The moveable member may abut a first reactive material. Unreacted material (34), chemically reactive with the either the first gas or the first reactive material to generate a second gas, is contained within the container. This apparatus also includes a reservoir of a liquid, adjacent to the moveable member in such a way that when the moveable member moves, the liquid is displaced out of the reservoir through a spout associated with the end of the container distal to the electrochemical cell. The reactive fluids are generally acids, bases, azides, and peroxides. The invention is useful for, among other things, the controlled delivery of medical fluids, fragrances, insecticides, and lubricants.

20 Claims, 4 Drawing Sheets

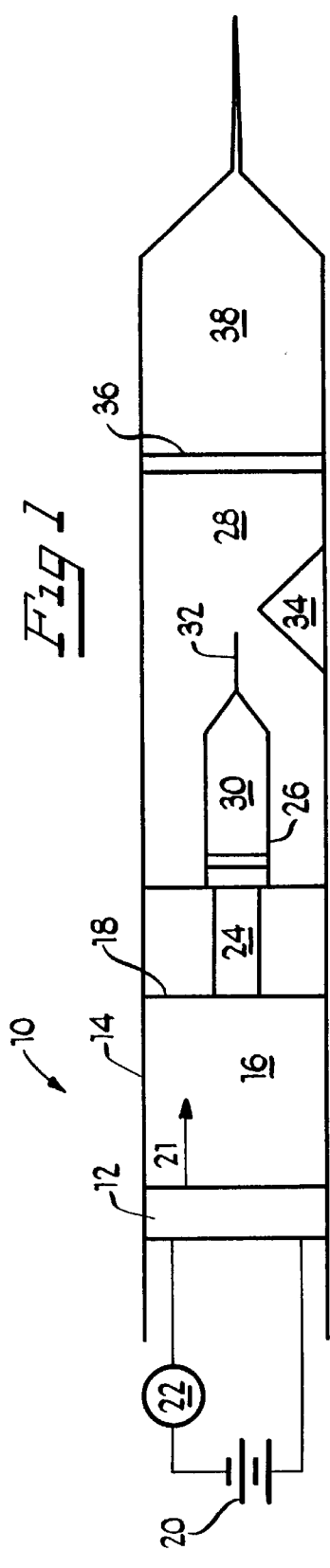
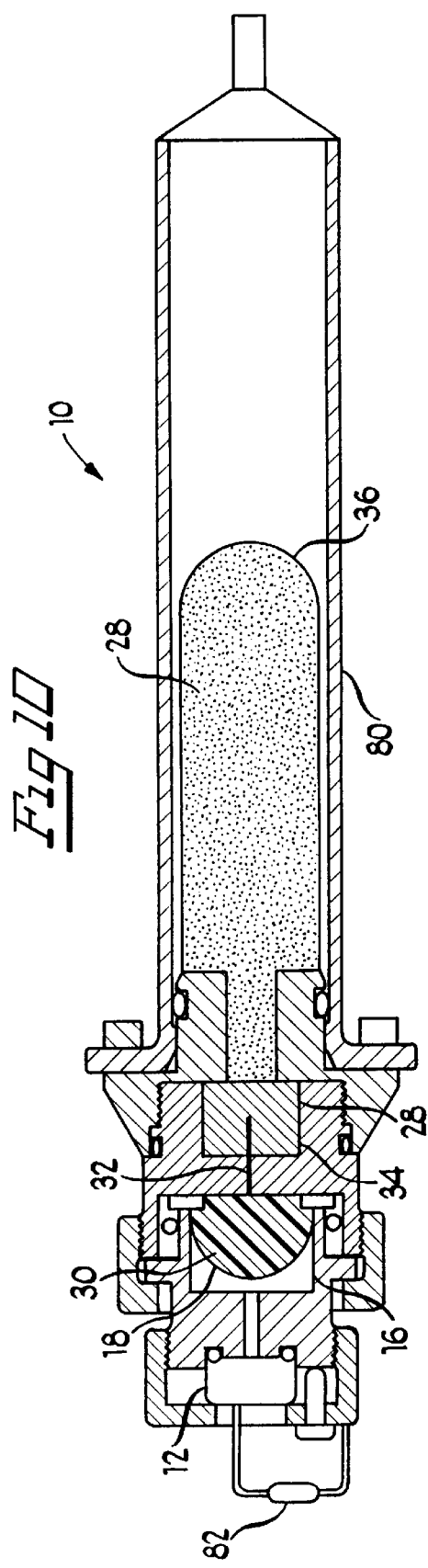

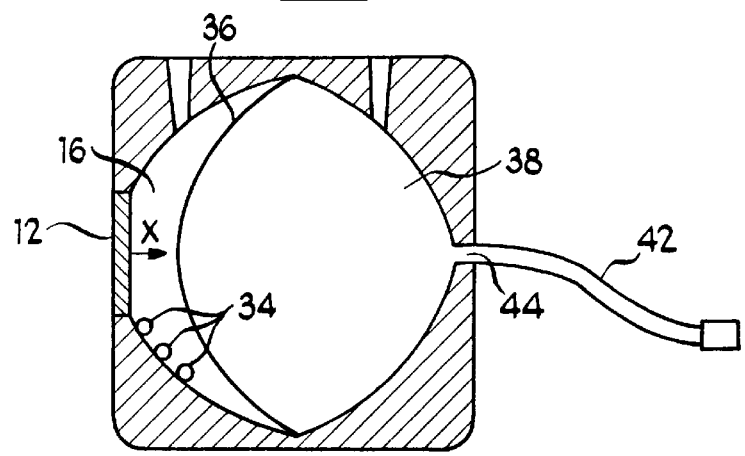
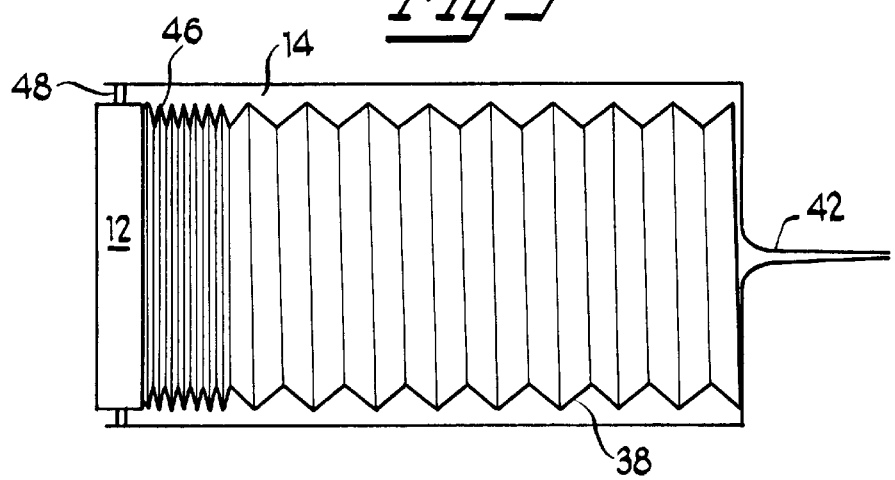
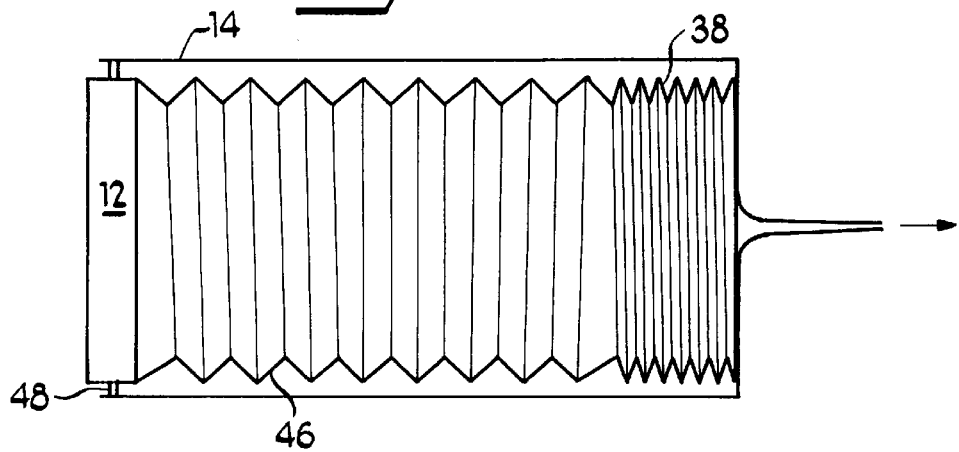

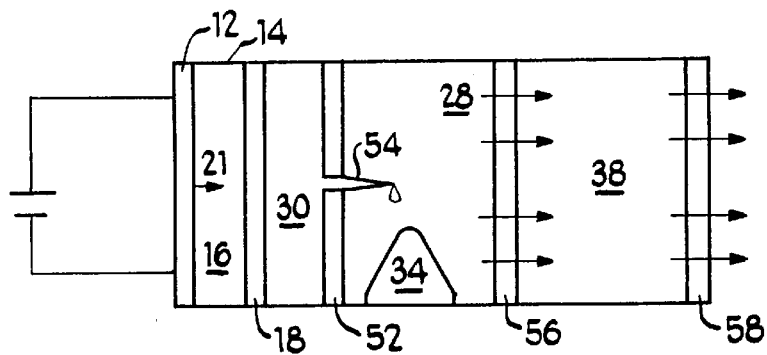
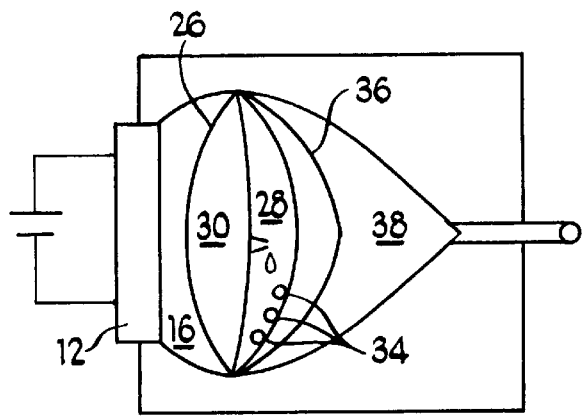
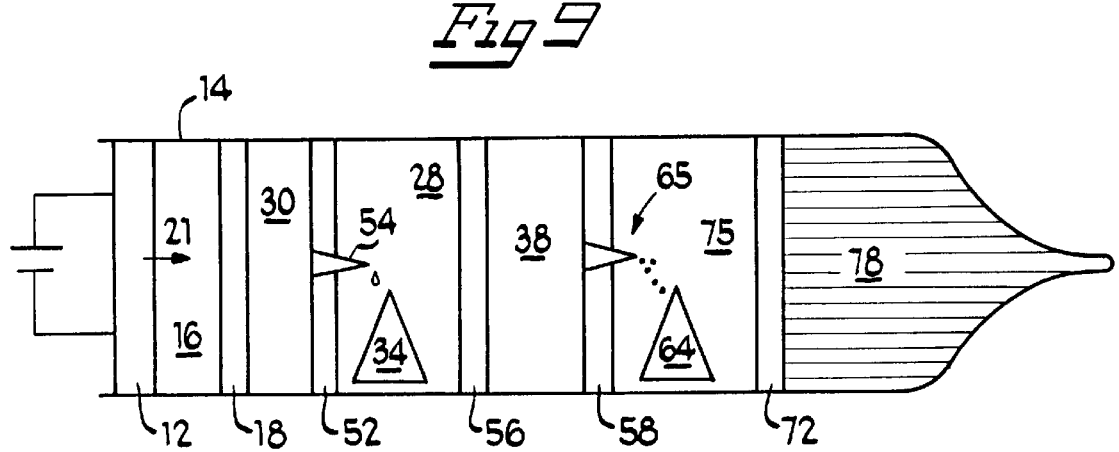

GAS AMPLIFIER

This application is a continuation of application Ser. No. 08/483,384 filed Jun. 7, 1995 which application is now abandoned.

TECHNICAL FIELD

The invention generally relates to methods and associated apparatus for controllably delivering fluids, and specifically to methods and apparatus for the controlled delivery of a liquid utilizing a first method of gas delivery to control chemical gas generation which generation may be used to deliver a fluid at a controlled rate (fixed and variable rate).

BACKGROUND

Devices which use an electrochemical pump to deliver a fixed quantity of liquid drug have been described. For example, U.S. Pat. No. 3,894,538 to Richter (Jul. 15, 1975) describes among other things a device for supplying medicines which includes a container having an opening for ejecting medicine therefrom, the container being associated with another container, the size of which can be increased by, for example, the generation of gas particles by electrolytical gas development within the container.

Somewhat similar devices are described in various patents to Maget. E.g. U.S. Pat. Nos. 4,522,698 to Maget (Jun. 11, 1985) and 4,902,278 to Maget et al. (Feb. 20, 1990).

A problem associated with such devices is that they require a relatively large amount of electrical energy to generate rather limited amounts of gas, which gas is used to displace the medicine containing liquid contained within the drug container or reservoir. Furthermore, the devices require relatively large amounts of energy to generate gas at a higher rate. It would be an improvement in the art to have a device which had the advantages (e.g. fine control of flow rate) of electrochemical gas generation to generate larger amounts of gases and/or higher rates of gas generation with fewer of the associated disadvantages (e.g. relatively large energy, power and space requirements).

DISCLOSURE OF THE INVENTION

The invention includes a very coulombically effective fluid delivery device utilizing a first, controllable method of gas delivery or production sequentially associated with at least one chemical gas production method.

The invention thus includes a fluid delivery device operated by a electrochemical pump using sequential electrochemical and chemical gas production methods. The device can be used to deliver a fluid in much greater quantities than the gas first produced.

The invention includes a fluid delivery device operated by a electrochemical pump using sequential electrochemical and chemical gas production methods.

The invention thus includes an apparatus for delivering a liquid or semisolid at a selected flow rate, the apparatus comprising container with an interior surface. An electrochemical cell for generating a first gas is placed in one end of the container. A moveable member (e.g. a piston, bellows, bladder or membrane) is positioned within the container, which moveable member, together with an adjacent surface of the electrochemical cell, generally structurally define a fluid-tight chamber. In one embodiment of the apparatus, unreacted material, chemically reactive with the first gas to produce a second gas, is contained within the container. The apparatus also includes a reservoir of a liquid, the reservoir associated with the moveable member in such a way that when the moveable member moves, the liquid is displaced out of the reservoir through an aperture associated with the end of the container distal to the electrochemical cell.

The invention can also include a gas-generating system which includes a gas generating structure for generating a quantity of a first gas (e.g. an electrochemical gas generating cell), a structural member displaceable by generation of the first gas, a fluid reactive material displaceable by the moveable member, and a second reactive material, reactive with the first fluid reactive material, to produce at least one gaseous reaction product.

The gas generating structure may generate the first gas in a substantially predetermined quantity at a substantially predetermined rate, and the liquid first reactive material may be present in a predetermined amount.

The gas generating system may further include a second moveable member in contact with (or containing) a dispensable fluid, the second moveable member being actuatable by the gaseous reaction product to displace the dispensable fluid (e.g. a medicine containing solution).

The invention also includes a gas generating device which includes (a) gas generating structure which generates at least a first gas, (b) a moveable member actuatable by production of the first gas, (c) a first chamber for holding a liquid reactive material, the first chamber being reducible in size by actuation of the moveable member, and having a vent or similar structure to permit liquid displaced therein to leave the first chamber, and (d) a second chamber in communication with the first vent, the second chamber sized and structured to hold a second reactive material which is reactive with the first liquid reactive material, and having a second vent for venting reaction products formed in the second chamber.

The invention still further includes a process that involves generating a first quantity of gas, displacing a fluid reactive material with the first quantity of gas to a reaction zone, and reacting the fluid reactive material with a second reactive material in the reaction zone wherein the reactive materials are selected to participate in a reaction which produces at least one reaction product.

The reactive fluids are generally acids, bases, azides, and peroxides. The reactive fluids preferably react with one another at substantially room temperature.

The disclosed apparatuses and methods are relatively inexpensive, and control over the delivery of large amounts of fluid can be achieved using a rather small device and control mechanism.

The invention is useful for, among other things, the controlled delivery of a biologically-active agent, such as the delivery of a drug to a subject, the delivery of an aroma to an environment, lubricant delivery, pesticide (e.g. insecticide) delivery, or for delivering a controlled amount of disinfectant.

BRIEF DESCRIPTION OF THE FIGURES

In the drawings, which depict presently preferred embodiments of the invention and in which like reference numerals refer to like parts:

FIG. 1 depicts a device useful in the practice of the invention.

FIG. 4 depicts an alternative embodiment of a device useful in the practice of the invention.

FIGS. 5 and 6 depict an alternative embodiment of a device useful in the practice of the invention.

FIG. 7 depicts an alternative embodiment of a device useful in the practice of the invention.

FIG. 8 depicts an alternative embodiment of a device useful in the practice of the invention.

FIG. 9 depicts an alternative embodiment of a device useful in the practice of the invention.

FIG. 10 depicts an alternative embodiment of a device useful in the practice of the invention.

BEST MODE OF THE INVENTION

Figure 2:
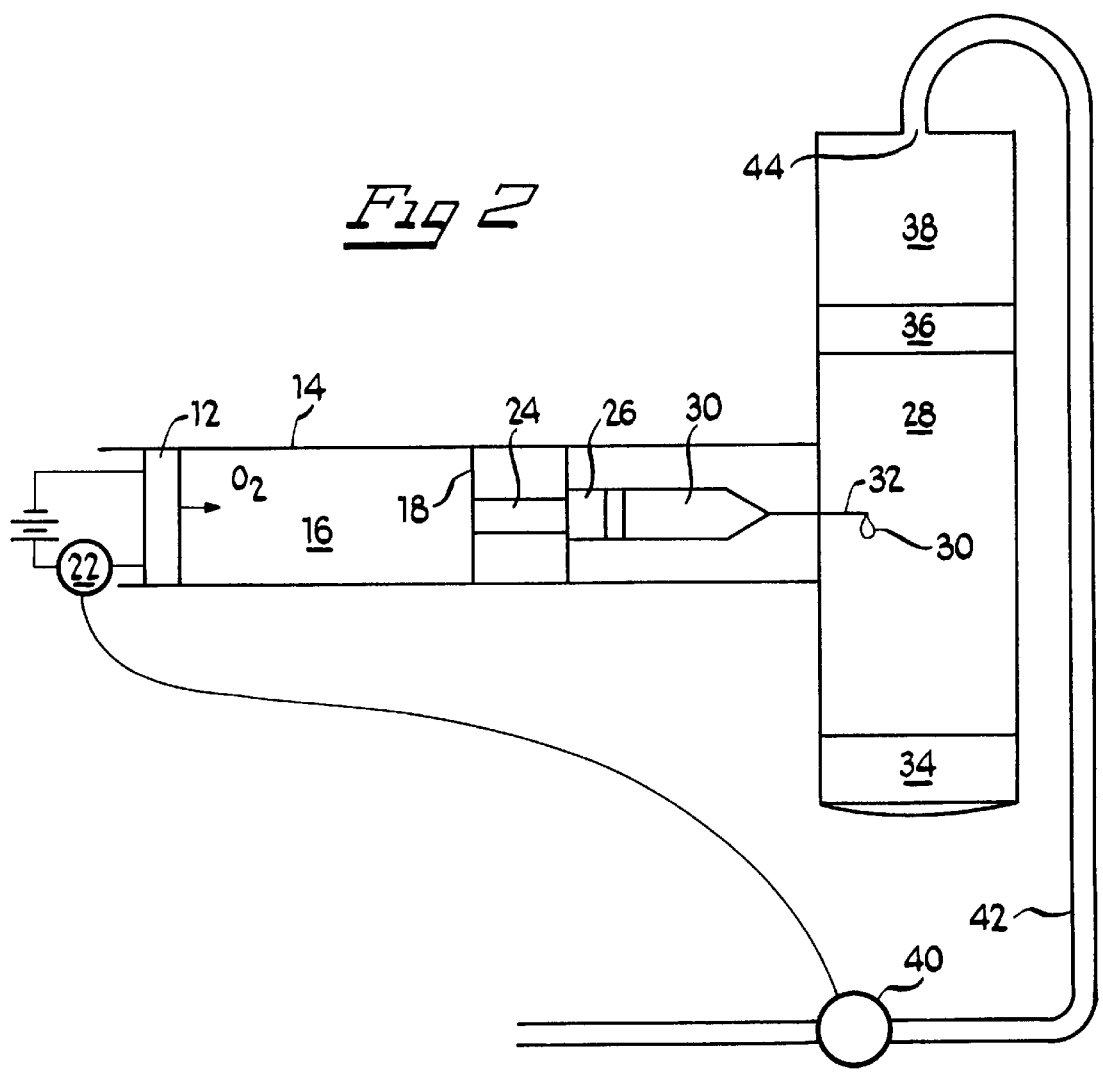
FIG. 2 depicts an alternative embodiment of a device useful in the practice of the invention.

As depicted in FIG. 1, the device, generally 10, includes an electrochemical gas generating cell 12 placed, in fluid tight arrangement within a portion of a cylinder 14. A first chamber 16 is defined by one surface of the electrochemical cell 12, a portion of the cylinder, and a surface of a piston 18 which moves within the cylinder 14.

Electrochemical cells capable of generating gases such as oxygen ($O_2$) hydrogen, nitrogen, halogen (e.g. $Cl_2$, bromine, iodine), carbon dioxide, and mixtures thereof are known. See, e.g., U.S. Pat. Nos. 4,402,817 and 4,522,698 which describe electrochemical cells. Such cells include solid polymer electrolyte-based oxygen or hydrogen generators, zinc-air type hydrogen gas generating batteries (see, e.g., U.S. Pat. No. 5,245,565 to Winsel (Sep. 7, 1993) or U.S. Pat. No. 4,023,648 to Orlitzky et al.), $Cu(OH)_2$ or carbonate-based oxygen generating cells, NaSiCON-based $CO_2/O_2$ generating cells (see, co-owned, co-pending application U.S. Ser. No. 08/413,635 filed on Mar. 30, 1995), or nitrogen generating batteries (see, e.g., co-owned, co-pending application U.S. Ser. No. 08/301,106 filed on Sep. 6, 1994, (U.S. Pat. No. 5,427,870 (Jun. 27, 1995)). The contents of all of these referenced patents and patent applications are incorporated by this reference.

As described in U.S. Pat. No. 4,902,278, a voltage gradient established across the electrochemical cell ionizes an electrochemically active material (e.g. atmospheric oxygen) at a electrode, transporting the ions through an electrolytic membrane to the other electrode, and reconverts the ions to molecules of the electrochemically active material which is evolved at the second electrode.

The cell 12 is powered by, for example, a battery 20, transformed direct current, fuel cell, or equivalent source of electricity. A circuit 22 is preferably placed in line for a user to control the amount of electrical energy to be applied to the cell 12, thus controlling the amount of gas generated by the cell 12. Such a circuit may include a galvanostat.

Gas is generated by the cell 12 (in the general direction of arrow 21) and passes into the first chamber 16. The first chamber 16 of FIG. 1 is itself fluid-tight, and gas transported into the chamber 16 from the cell 12 increases the pressure in the chamber 16. In the embodiment depicted in FIG. 1, as the pressure within the first chamber 16 increases, the piston 18 moves inside the cylinder in a direction opposite that of the cell. In a preferred embodiment, the piston 18 moves unidirectionally away from the cell 12 within the cylinder 14, which can be accomplished by the use of certain single-use syringes. In the embodiment depicted in FIG. 1, the piston is a portion of a plunger 24 associated with a syringe 26 and serves to distinguish the first chamber 16 from a second chamber 28.

Contained within the syringe 26 is a reactive fluid 30. Proximate the spout end 32 of the syringe 26 is a material 34 capable of reacting with the reactive fluid 30. The reactive fluid 30 and material 34 are selected to be compounds which, when they come into contact with one another, generate a gaseous species. For example, the reactive fluid 30 may be an acidic material, such as hydrochloric or other acid, in which case, the material 34 could be zinc metal (to generate hydrogen gas when reacted with the HCl or citric acid) or a basic material such as sodium bicarbonate (to generate carbon dioxide when reacted with the HCl or citric acid).

Acids useful in practicing the invention include acids such as citric, hydrochloric, sulfuric, phosphoric, acetic, nitric, propionic, succinic, fumaric, maleic, citric, tartaric, cinnamic, lactic, mandelic, ethanedisulfonic acid, equivalents of these acids, and mixtures thereof.

Bases useful for practicing the invention include metal bicarbonates (e.g. $NaHCO_3$), metal carbonates (e.g. $Na_2CO_3$), and other bases.

Preferred reaction pairs include metal bicarbonates and organic acids, water and an effervescent powder (e.g. ALKA SELTZER™), peroxides and water, azides and water, azides and metal halide solutions, and lithium and water.

Alternatively, chemical reactants such as azides (e.g. $NaN_3$), peroxides, $NaO_2$, $KO_2$, sodium carbonate, and mixtures thereof may be used.

Specifically preferred reaction pairs include:

(i) $NaHCO_3$+citric acid→sodium citrate+$CO_2(\uparrow)$+$H_2O$, (ii) $Na_2CO_3$+citric acid→sodium citrate+$CO_2(\uparrow)$+$H_2O$, (iii) $2KO_2+H_2O \rightarrow 2KOH+3/2O_2(\uparrow)$:superoxides and water), (iv) $2Li+H_2O \rightarrow Li_2O+H_2(\uparrow)$:(metal and water), (v) $2Al+6HCl \rightarrow 2AlCl_3+3H_2(\uparrow)$:(metal and acid), (vi) $Zn+H_2O \rightarrow ZnO+H_2(\uparrow)$:(metal and aqueous solution), (vii) $Mg_2+H_2O \rightarrow MgO+2H_2(\uparrow)$:(metal hydride and water), (viii) $NaN_3+H_2O \rightarrow NaOH+N_2(\uparrow)$:(azide and water)

(ix) $2NaN_3+I_2 \rightarrow 2NaI+3N_2(\uparrow)$:(azide and iodine)

(x) catalyst+$H_2O_2 \rightarrow H_2O+O_2(\uparrow)$:(peroxide and enzyme).

The increased pressure generated in the first chamber 16 drives the plunger within the syringe 26 driving out a small amount of first reactive liquid 30 through the spout 32 (or associated needle) dripping the first reactive fluid onto the material 34. The two compounds 30, 34 react, generating a gas product in second chamber 28. Such reaction products increase the pressure in chamber 28 driving a second piston 36 also in fluid tight arrangement with the cylinder 14.

In one embodiment (not shown), the second chamber is associated with a heating element to further amplify the volume of gas present in the chamber.

Second piston 36 is in fluid communication with a reservoir 38 of liquid material (e.g. pharmacologically active solution) to be delivered in a controlled quantity at a controlled rate.

FIG. 2 depicts another embodiment of the invention. In this embodiment, the second chamber 28; reactive material 34, second piston 36, and reservoir 38 are not contained within cylinder 14. Furthermore, a flow meter 40 is associated with the tubing 42 leading from the aperture 44 associated with the reservoir 38. This flow meter 40 (optionally a flow restrictor flow meter) is associated (e.g. electrically or pneumatically) with the control circuit 22. If the flow rate of liquid through the tube 42 should decrease or increase beyond a predetermined range, the control circuit 22 increases or decreases the amount of electricity passing through the electrochemical cell 12 thus generating more or less of the first gas to the first chamber thus altering the flow rate appropriately. Alternatively, a pressure sensor may be associated with the first or second chamber (not shown). The circuit may also be computer-controlled to deliver predetermined amounts of liquid from the reservoir at predetermined times.

Devices incorporating several sequential chambers of chemical gas generating equipment may also be utilized (not shown).

Figure 3:
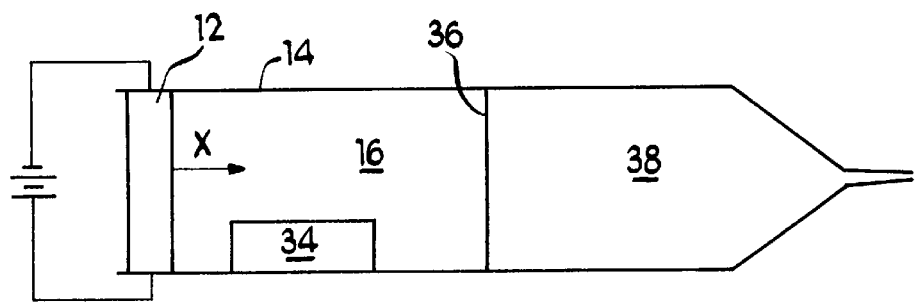
FIG. 3 depicts an alternative embodiment of a device useful in the practice of the invention.

FIG. 3 depicts still another embodiment of the invention. In this embodiment, gaseous species "X" (e.g. $O_2$) is generated by cell 12 which cell is fixedly placed within a cylinder 14 (e.g. by a epoxy or glass seal circumscribing the cell and sealing it to the interior of the cylinder). An electrical potential is applied to the cell 12, and a selected gaseous species is generated. The thus generated gaseous species reacts with an amount of reactive material 34 (e.g. $NaN_3$ in the case where gaseous species X is $O_2$) present in the chamber 16 to generate a gas (e.g. $4NaN_3+O_2 \rightarrow 2 Na_2O+6N_2$). The pressure increase causes movement of piston 36 (which piston further defines) away from the cell 12. In the embodiment depicted in FIG. 3, the piston 36 is directly associated with a reservoir of liquid material to be delivered.

Other reactant materials may be used in place of oxygen and azide. For instance a cell which generates a halogen such as chlorine may be substituted for an oxygen generating cell (e.g. $4NaN_3+2Cl_2 \rightarrow 2NaCl+3N_2$). Also, the $NaN_3$ may be substituted with (or supplemented with) a pellet of $BaO_2$.

The apparatus can also incorporate a properly placed catalyst selected from the group consisting of high surface area silica, $Al_2O_3$, noble metals, and mixtures thereof, In an alternative embodiment of the device of FIG. 3 (not shown) the piston is indirectly associated with the reservoir of liquid material to be delivered indirectly by a syringe plunger.

FIG. 4 depicts a device which operates in a manner similar to the device depicted in FIG. 3, except that an elastomeric membrane 36' is used in place of piston 36 of FIG. 3.

FIGS. 5 and 6 depict another device wherein the electrochemical cell 12 is not necessarily sealed within the container 14. Instead, a first bellows-type bladder 46 is fluidically sealed to the gas-generating side of the electrochemical cell 12 which thus defines the first chamber. The electrochemical cell may be sealed to the container, may be fixedly attached to the container 14 (e.g. by pins 48, screws, welds, etc.), or may fit loosely within the container and, when the bellows fills with gas, be driven against a screen or other retaining member associated with the end of the container. Inside this bladder 46 is contained the unreacted material (not shown), reactive with the gas brought into the chamber by the electrochemical cell 12 to generate a gas. In the embodiment depicted in FIGS. 5 and 6, a second bellows-type bladder 50 is used to contain the reservoir of liquid to be delivered. Both of the bladders are non-porous.

When gas is generated by the electrochemical cell 12, that gas reacts with the unreacted reactive material contained within the first bladder 46, amplifying the amount of gas generated, thus inflating the first bladder 46. As the first bladder 46 inflates, it expands, abuts (either directly or indirectly), and compresses the second bladder 50 contained within the container 14 (FIG. 6). As the second bladder compresses, it delivers the liquid contained within the reservoir.

Medicaments useful for delivery with the device include chemical and biological agents which are to be delivered over a period of time at a set or variable rate. Such agents include antiarrhythmic, antibiotics, sedatives, proteins such as insulin, and other agents.

The materials used in constructing the components of the invention will be selected to be compatible with the various reactants and products.

The invention is further explained by the following illustrative EXAMPLES.

EXAMPLES

Example I

A device is built as depicted in FIG. 1. The electrochemical cell 12 is made of polymeric electrolyte based $O_2$ generating cell (e.g. that described in U.S. Pat. Nos. 4,522, 698 and 4,902,278 to Maget) and is powered by a direct current voltage source (e.g. a battery). The reactive fluid 30 contained within the syringe is a 20% HCl aqueous solution. The unreacted material 34 is $NaHCO_3$. For every 36.5 g of 100% HCl used in the reaction, 22.4 liters of $CO_2$ is generated (at room temp.). For every 1 cc of gas produced at the electrochemical cell, 1 cc of 20% HCl solution reacts with $NaHCO_3$. (according to the following reaction:

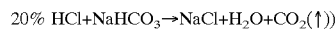

20% $HCl+NaHCO_3 \rightarrow NaCl+H_2O+CO_2(\uparrow)$))

and 123 cc of gas are produced in the second chamber 28, displacing 123 cc of medicament (e.g. lidocaine) solution.

Example II

A device is built as depicted in FIG. 2. The electrochemical cell 12 is made of NASICON based ($CO_2+O_2$) generating cell (e.g. co-owned, co-pending application U.S. Ser. No. 08/413,635 filed Mar. 30, 1995) and is powered by a direct current power source. The reactive fluid contained within the syringe 30 is citric acid. The unreacted reactive material 34 is $NaHCO_3$. For each 1 cc gas produced at the electrochemical cell, 1 cc of citric acid solution ($H_3C_6H_5O_7$ (aq)) containing 0.5 g of citric acid reacts with $NaHCO_3$ and 172 cc of $CO_2(g)$ in second chamber 28 displacing 172 cc of fluid. The reaction is as follows $2H_3C_6H_5O_7+6Na HCO_3+ 5H_2O \rightarrow 2Na_3C_5O.11H_2O+6CO_2\uparrow$.

EXAMPLE III

A device is built as depicted in FIG. 1. The electrochemical cell 12 is zinc-air type hydrogen generator, and is thus self-powered. The reactive material contained within the syringe is 20% $ZnCl_2$ solution. The unreacted material 34 is $NaN_3$. For each 1 cc of gas produced at the electrochemical cell, 1 cc of 20% $ZnCl_2$ reacts with $NaN_3$ and 100 cc of nitrogen gas is produced according to the following reaction:

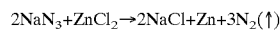

$2NaN_3+ZnCl_2 \rightarrow 2NaCl+Zn+3N_2(\uparrow)$ displacing 100 cc of medicament solution.

Example IV

A device is built as depicted in FIG. 3. The electrochemical cell 12 is a chlorine gas generator. The chlorine gas thus generated reacts with unacted material 34. The unreacted material 34 is $NaO_2$. For each one (1) cc of chlorine gas produced at the electrochemical cell, two (2) cc of oxygen gas are produced in the chamber 16, displacing two (2) cc of aromatic solution contained within chamber 38. The reaction proceeds according to the following:

$$2NaO_2 + Cl_2 \rightarrow + 2O_2(\uparrow)$$

Example V

A device is built as depicted in FIG. 4. The electrochemical cell 12 is a chlorine gas generator. The chlorine gas thus generated reacts with unreacted material 34. The unreacted material 34 is $NaN_3$. For each one (1) cc of chlorine gas produced at the electrochemical cell, three (3) cc of nitrogen gas are produced in the chamber 16, displacing three (3) cc of aromatic solution contained within chamber 38. The reaction proceeds according to the following:

$$2NaN_3 + Cl_2 \rightarrow + 3N_2(\uparrow)$$

Example VI

A device is built as depicted in FIGS. 5 and 6. The electrochemical cell 12 is made of a gas generating cell, and is powered by a button cell battery. The unreacted material 34 is calcium. Gas produced at the electrochemical cell, through the depicted system displaces a light mineral oil lubricant.

Example VII

A device is built as depicted in FIG. 7. In the depicted device, a battery provides electrical energy for the cell 12. The cell 12 generates a gas (in the general direction of arrow 21). The pressure contained within the first chamber 16 defined by the cell 12, container 14, and piston 18 increases, moving piston 18 towards a rigid plate 52 also placed within the container 14. Extending through the rigid plate is an aperture 52. Contained between the piston 18, the rigid plate 50, and the interior surface of the container 14 is a reservoir of first reactive fluid 30. As the piston 18 moves, it displaces the reactive fluid 30 which is driven out of the aperture 52, to react with reactive material 34 situated proximate the aperture 52 so that the reactive fluid will react with the reactive material 34 to generate a gas. The thus generated gas (e.g. $CO_2$) then passes through a first gas permeable membrane 56. The gas permeable membrane helps to contain a reservoir 38 of, for example, fragrance containing liquid. A second gas permeable membrane 58 also helps to contain the reservoir 38. As gas permeates the first gas permeable membrane 56, it acts to drive out the fragrance contained within the reservoir through the second gas permeable membrane 58.

Example VIII

A device is built as depicted in FIG. 8. The gas producing cell 12 is a chemical gas producing cell (such as metallic zinc and an aqueous solution of salts, acids and bases) whereby hydrogen gas is produced at a predetermined rate and quantity. This gas cell is activated by breaking a seal which exists between the zinc and the aqueous solution. The $H_2$ so generated moves the diaphragm 26 pushing the reactive fluid 30 (e.g. citric acid) onto reactive solid 34 (e.g. $Na_2CO_3$) to form carbon dioxide gas in chamber 28. The $CO_2$ so formed in turn pushes the diaphragm 36 thus dispensing fluid from chamber 38.

Example IX

A device is built as depicted in FIG. 2. The electrochemical cell 12 is made of a solid polymer electrolyte based oxygen or hydrogen generation cell, and is powered by a direct current power source. The reactive fluid contained within the syringe 30 is HCl. The unreacted reactive material 34 is zinc. For each 1 cc gas produced at the electrochemical cell, 1 cc of 20% HCl solution is reacted with zinc according to the reaction:

$$Zn + HCl \rightarrow + H_2(\uparrow) + ZnCl_2$$

60 cc of hydrogen gas are produced in second chamber 28 displacing 60 cc of solution 38.

Example X

A device is built as depicted in FIG. 3. The electrochemical cell 12 is made of electrodes producing oxygen and hydrogen gas and is powered by a D.C. power source transformed from an A.C. current. The reactive material contained within the syringe is a citric acid solution. The unreacted material 34 is $Na_2CO_3$. For each 1 cc of gas produced at the electrochemical cell, 1 cc of citric acid reacts with $Na_2CO_3$ and eighty-six (86) cc of carbon dioxide gas is produced according to the following reaction:

$$2H_3C_6H_5O_7(solution) + Na_2CO_3 \rightarrow 2Na_3C_6H_5O_7(solution) + 3H_2O + 3CO_2(\uparrow)$$

displacing eighty-six (86) cc of medicament solution.

Example XI

A device is built as depicted in FIG. 2. The electrochemical cell 12 is a Zn-air type hydrogen generating cell and is self-powered. The reactive fluid 30 is water. The oxygen gas thus generated reacts with unreacted material 34. The unreacted material 34 is LiH. For each one (1) cc of oxygen gas produced at the electrochemical cell, one (1) cc of water is displaced onto LiH to generate approximately 2375 cc of $H_2$ gas, displacing an equivalent amount of fluid from chamber 38. The reaction proceeds according to the following:

$$2LiH + H_2O \rightarrow + Li_2O + 2H_2(\uparrow)$$

Example XII

A device is built as depicted in FIG. 4. The electrochemical cell 12 is either $O_2$, $H_2$, or a $CO_2 + O_2$ generator, and is powered by a battery. The fluid in compartment 30 is water. The displaced water reacts with KO2 to produce $O_2$ gas. The unreacted material 34 is $KO_2$. For each 1 cc of gas produced at the electrochemical cell, 933 cc of $O_2$ gas is produced in the chamber 16, displacing 933 cc of a light mineral oil lubricant. The reaction proceeds according to the following:

$$2KO_2 + 2H_2O \rightarrow + 2KOH + H_2O + 3/2O_2(\uparrow)$$

Example XIII

In EXAMPLE XII, 933 cc of $O_2$ is produced. In electrochemistry, one ampere-hour of energy produces 210 cc of $O_2$ at standard temperature and pressure. Therefore, to generate 933 cc, about 4.42 amp-hr are required. With the invention however, only 4.76 milliamp-hrs are required to generate 1 cc of gas to generate on the order of 3 orders of volume of oxygen gas.

Example XIV

A device built as depicted in FIG. 9. The electrochemical cell can be polymeric solid. The electrolyte based $O_2$ generalize cell is powered by a button cell battery. The reactive fluid contained within compartment 30 is citric acid. The chemical 34 is sodium bicarbonate. The movable piston 56 dispenses citric acid contained in chamber 38. The movable piston 72, under gas generated in chamber 75, delivers the fluid contained in chamber 78. For each 1 cc of gas produced at the electrochemical cell, 1 cc of citric acid contained in chamber 30 is dispensed onto sodium bicarbonate to generate 172 cc of $CO_2$ gas. This 172 cc of gas produced in chamber 28 pushes piston 56 to deliver 172 cc of citric acid contained in chamber 38 onto $NaHCO_3$ (64) contained in chamber 75. The total gas produced in chamber 75 is 29,584 cc which moves piston 72 and delivers 29,584 cc of fluid contained in chamber 78.

Example XV

A device was built as depicted in FIG. 10. To initially generate gas it used a polymer-type E-cell 12 having the capacity to produce only nine cc's of gas. The device was designed to produce a large amount of $CO_2$ gas by pumping a small amount of citric acid 30 onto sodium carbonate 34. The entire contents of a thirty (30) cc syringe 80 was expelled from the syringe in a matter of hours using the tiny, but very flat output of a standard polymer E-cell.

To achieve this result, first, the bladder cavity 30 was filled with a 33% citric acid solution. The reaction chamber 28 was filled with a slurry of sodium carbonate and water. The small inside diameter of the tube 32 between the chambers 16, 28 prevented mixing of the reactive materials without pressure being applied to the bladder 18. Next, this portion of the apparatus was connected to the syringe 80 filled with water. A second bladder 36 separated the body of the syringe from the remainder of the apparatus. Finally, a standard E-cell was inserted into the apparatus. A twenty (20) ohm resistor (82) was attached between the can and cap to start the E-cell.

As the E-cell pumped oxygen into the bladder chamber 16, the oxygen moved the bladder 18 towards the reaction chamber 28. This pushed the citric acid solution 30 at a controlled rate through the tube 32 and into the reaction chamber 28. There, it reacted with the sodium carbonate 34 to form $CO_2$ gas at a controlled rate. The $CO_2$ gas then expanded into syringe bladder 36, displacing liquid (water) from the syringe 80 at a controlled rate many times that of the E-cell's output. The bladder 36 filled to its full capacity, and continued to stretch until it filled the entire volume of the thirty (30) cc syringe displacing the liquid.

Although the invention has been described with regard to certain preferred embodiments, the scope of the invention is to be defined by the appended claims.

What is claimed is:

1. A fluid delivery apparatus comprising:
   a source for a first reagent;
   a reaction chamber;
   means for positioning the first reagent source into the reaction chamber;
   means for controllably generating a first gas into the reaction chamber;
   means operatively associated with the reaction chamber for reacting the first reagent source with the first gas, to, in turn, controllably generating a second gas upon introduction and reaction with the first gas; and
   a fluid dispensing chamber associated with the reaction chamber, wherein the fluid dispensing chamber includes a movable member controllably movable by the second gas.

2. The fluid delivery apparatus according to claim 1, wherein the first gas generating means includes an electrochemical cell.

3. The fluid delivery apparatus according to claim 2, wherein the electrochemical cell is associated with a control circuit to regulate the generation of the first gas.

4. The fluid delivery apparatus according to claim 3, wherein the control circuit is associated with a monitoring device associated with at least one of the reaction chamber and fluid dispensing chamber.

5. The fluid delivery apparatus according to claim 1, wherein the means for controllably generating the second gas comprises the first gas generating means and a chemical reagent.

6. The fluid delivery apparatus according to claim 5, wherein the chemical reagent is selected from the group of azides, peroxides, nitrides, carbonates, bicarbonates and mixtures thereof.

7. The fluid delivery apparatus according to claim 1, wherein the fluid dispensing chamber includes a fluid.

8. The fluid delivery apparatus according to claim 7, wherein the fluid is selected from the group of medicinal products, lubricants, disinfectants, deodorants, pesticides, and insecticides.

9. A fluid delivery apparatus comprising:
   a gas chamber;
   means for controllably generating a first gas into the gas chamber;
   a source for a first fluid;
   a first fluid dispensing chamber associated with the gas chamber, wherein the first fluid dispensing chamber includes a movable member controllably movable by the first gas;
   means for associating the first fluid source within the first fluid dispensing chamber;
   a reaction chamber associated with the first fluid dispensing chamber, wherein movement of the movable member dispenses fluid from the first fluid dispensing chamber into the reaction chamber;
   a source for a first reagent;
   means for positioning the first reagent source within the reaction chamber;
   means operatively associated with the reaction chamber for for reacting the first reagent with the first gas, and, in turn, controllably generating a second gas upon introduction of the first gas and reaction thereof with the first fluid;
   a source for a second fluid;
   means for positioning the second fluid source within the second fluid dispensing chamber; and
   a second fluid dispensing chamber associated with the reaction chamber, wherein the second fluid dispensing chamber includes a movable member controllably movable by the second gas.

10. The fluid delivery apparatus according to claim 9, wherein the first gas generating means comprises an electrochemical cell.

11. The fluid delivery apparatus according to claim 10, wherein the electrochemical cell is associated with a control circuit to regulate the generation of at least the first gas.

12. The fluid delivery apparatus according to claim 11, wherein the control circuit is associated with a monitoring device associated with at least one of the gas chamber, the first fluid dispensing chamber, the reaction chamber, and the second fluid dispensing chamber.

13. The fluid delivery apparatus according to claim 9, wherein the means for controllably generating a second gas comprises a first chemical reagent releasably retained in the first fluid dispensing chamber and a second chemical reagent.

14. The fluid delivery apparatus according to claim 13, wherein the first chemical reagent is selected from the group of azides, nitrides, peroxides, carbonates, bicarbonates and mixtures thereof and the second chemical reagent is selected from fluids which will react with the first chemical reagent to produce a gas.

15. The fluid delivery apparatus according to claim 13, wherein the first chemical reagent is an acid.

16. The fluid delivery apparatus according to claim 13, wherein the second chemical reagent is a base.

17. The fluid delivery apparatus according to claim 13, wherein the second chemical reagent is selected from the group of reactive metals, metal oxides, carbonates, bicarbonates and mixtures, solutions, and slurries thereof.

18. The fluid delivery apparatus according to claim 13, wherein the first chemical reagent is a base and the second chemical reagent is an acid.

19. The fluid delivery apparatus according to claim 9, wherein the second fluid dispensing chamber includes a fluid.

20. The fluid delivery apparatus according to claim 19, wherein the fluid is selected from the group of medicinal products, lubricants, disinfectants, deodorants, pesticides, and insecticides.

* * * * *